(12) United States Patent
Liu et al.

(10) Patent No.: US 8,603,247 B2
(45) Date of Patent: Dec. 10, 2013

(54) APPARATUS FOR COUNTING PARTICLES IN A GAS

(71) Applicant: MSP Corporation, Shoreview, MN (US)

(72) Inventors: Benjamin Y. H. Liu, North Oaks, MN (US); Thuc M. Dinh, Shakopee, MN (US); William D. Dick, Minneapolis, MN (US); Aaron M. Collins, Minneapolis, MN (US); Francisco J. Romay, Vadnais Heights, MN (US)

(73) Assignee: MSP Corporation, Shoreview, MN (US)

( * ) Notice: Subject to any disclaimer, the term of this patent is extended or adjusted under 35 U.S.C. 154(b) by 0 days.

(21) Appl. No.: 13/887,554

(22) Filed: May 6, 2013

(65) Prior Publication Data
US 2013/0239888 A1  Sep. 19, 2013

Related U.S. Application Data

(62) Division of application No. 13/603,693, filed on Sep. 5, 2012, which is a division of application No. 12/872,697, filed on Aug. 31, 2010, now Pat. No. 8,465,791.

(60) Provisional application No. 61/252,243, filed on Oct. 16, 2009.

(51) Int. Cl.
C23C 16/448  (2006.01)
C23C 16/455  (2006.01)
C23C 16/52   (2006.01)

(52) U.S. Cl.
USPC .............................. 118/726; 118/715; 356/37

(58) Field of Classification Search
USPC ....................................... 118/715, 726; 356/37
See application file for complete search history.

(56) References Cited

U.S. PATENT DOCUMENTS

| 3,570,826 | A | * | 3/1971 | Bergson ......................... 204/233 |
| 4,449,816 | A |   | 5/1984 | Kohsaka et al. |
| 4,790,650 | A |   | 12/1988 | Keady |
| 5,239,356 | A | * | 8/1993 | Hollander et al. ............... 356/37 |
| 5,711,816 | A | * | 1/1998 | Kirlin et al. ..................... 118/726 |
| 5,803,338 | A |   | 9/1998 | Singer et al. |
| 5,849,089 | A | * | 12/1998 | Tsunashima et al. ......... 118/726 |
| 6,567,157 | B1 |  | 5/2003 | Flagan et al. |
| 6,712,881 | B2 |  | 3/2004 | Hering et al. |
| 6,829,044 | B2 |  | 12/2004 | Liu |
| 6,980,284 | B2 |  | 12/2005 | Ahn et al. |
| 7,497,420 | B2 | * | 3/2009 | Soininen ........................ 261/104 |
| 8,066,852 | B2 | * | 11/2011 | Yang et al. ....................... 203/39 |
| 8,105,423 | B2 | * | 1/2012 | Alper ............................... 95/285 |

(Continued)

OTHER PUBLICATIONS

PCT International Search Report, May 24, 2011.

(Continued)

Primary Examiner — Jeffrie R Lund
(74) Attorney, Agent, or Firm — Westman, Champlin & Koehler, PA; Z. Peter Sawicki

(57) ABSTRACT

The present disclosure describes an apparatus for detecting particles in a gas by saturating the gas with vapor and causing the gas to flow through a chamber with walls that are at a temperature different than the temperature of the entering gas creating a gas turbulence within the chamber resulting in the gas becoming super-saturated with vapor and causing said super-saturated vapor to condense on said particles and form droplets, which are then detected and counted by an optical light-scattering detector.

6 Claims, 13 Drawing Sheets

(56) References Cited

U.S. PATENT DOCUMENTS

| | | | |
|---|---|---|---|
| 8,297,223 B2* | 10/2012 | Liu et al. | 118/723 VE |
| 8,465,791 B2* | 6/2013 | Liu et al. | 427/8 |
| 2003/0202169 A1* | 10/2003 | Liu | 356/37 |
| 2004/0012772 A1* | 1/2004 | Ahn et al. | 356/37 |
| 2004/0139853 A1* | 7/2004 | Bologa et al. | 95/64 |
| 2005/0147749 A1* | 7/2005 | Liu et al. | 427/248.1 |
| 2007/0120275 A1* | 5/2007 | Liu | 261/100 |
| 2007/0242261 A1 | 10/2007 | Liu | |
| 2008/0137065 A1* | 6/2008 | Oberreit et al. | 356/37 |
| 2008/0144003 A1* | 6/2008 | Blackford et al. | 356/37 |
| 2008/0152547 A1 | 6/2008 | Hopke et al. | |
| 2009/0009748 A1* | 1/2009 | Ahn | 356/37 |
| 2009/0009749 A1* | 1/2009 | Ahn | 356/37 |
| 2009/0084315 A1* | 4/2009 | Liu et al. | 118/715 |
| 2009/0133632 A1* | 5/2009 | Soininen | 118/726 |
| 2009/0283041 A1* | 11/2009 | Tomiyasu et al. | 118/726 |
| 2010/0213050 A1* | 8/2010 | McAlister | 204/252 |
| 2010/0213076 A1* | 8/2010 | McAlister | 205/637 |
| 2010/0263731 A1* | 10/2010 | Hopke et al. | 137/1 |
| 2011/0091649 A1* | 4/2011 | Liu et al. | 427/255.25 |
| 2012/0229795 A1* | 9/2012 | Hopke et al. | 356/37 |
| 2013/0036973 A1* | 2/2013 | Liu et al. | 118/712 |

OTHER PUBLICATIONS

PCT Written Opinion, May 24, 2011.

* cited by examiner

APPARATUS FOR COUNTING PARTICLES IN A GAS

CROSS-REFERENCE TO RELATED APPLICATION

The present application is a divisional application of U.S. patent application Ser. No. 13/603,693, filed Sep. 5, 2012, which is a divisional application of U.S. patent application Ser. No. 12/872,697, filed Aug. 31, 2010 which is based on and claims the benefit of U.S. provisional patent application Ser. No. 61/252,243, filed Oct. 16, 2009, the contents of which are hereby incorporated by reference in their entirety.

BACKGROUND OF THE DISCLOSURE

The present disclosure describes a method and an apparatus for detecting particles in a gas by condensing vapor on the particles to form droplets, which are then detected by an optical, light-scattering detector. Instruments using vapor condensation on particles to form droplets for detection are referred to as condensation particle counters (CPC), or as condensation nucleus counters (CNC). A variety of working fluids can be used to generate vapor for condensation. The most common working fluids are butyl alcohol and water.

Condensation particle counters are useful in many applications. In air pollution and climate research, for instance, the instrument is often used with an electrical mobility analyzer to determine the concentration and size distribution of particles in the ambient atmosphere. The instrument can also be used to detect particulate contaminants suspended in clean-room air for clean-room monitoring and contamination control purposes. In addition, CPC is widely used in laboratory research to study the property and behavior of small airborne particles.

The most important process in a CPC is the process of vapor generation, condensation and droplet growth. The present disclosure describes a new approach to creating super-saturation for vapor condensation and droplet growth, leading to a compact measuring device with improved performance characteristics.

SUMMARY OF THE DISCLOSURE

The present disclosure describes a method and apparatus for detecting particles in a gas by saturating the gas with vapor at one temperature and causing the gas to flow through a chamber with walls at a different temperature, thereby changing the gas temperature in the chamber. At the same time the gas flow is made turbulent causing the gas to mix in the chamber to create super-saturation for vapor to condense on said particles and form droplets, which are then detected and counted by an optical light-scattering detector.

DESCRIPTION OF THE EMBODIMENTS

Figure 1:
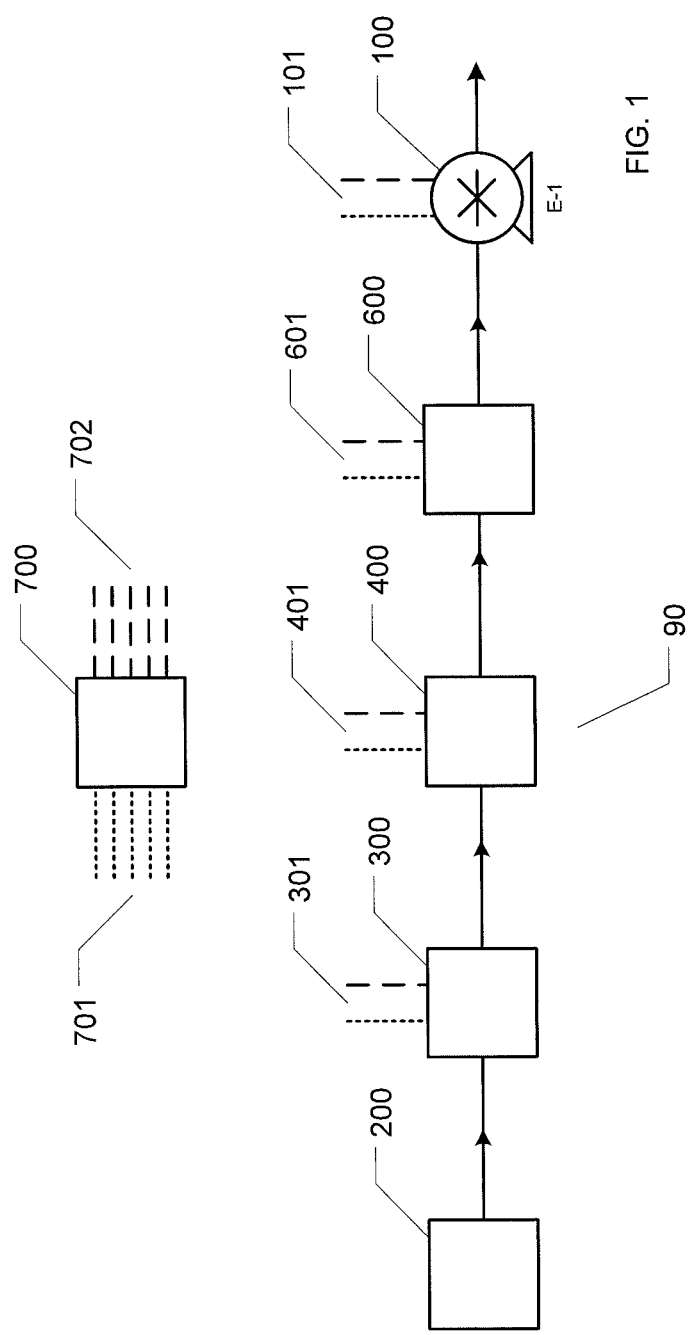
FIG. 1 is a schematic diagram of the system for detecting particles in a gas by vapor condensation on particles to form droplets and detecting the droplets so formed by an optical light-scattering detector.
Figure 2:
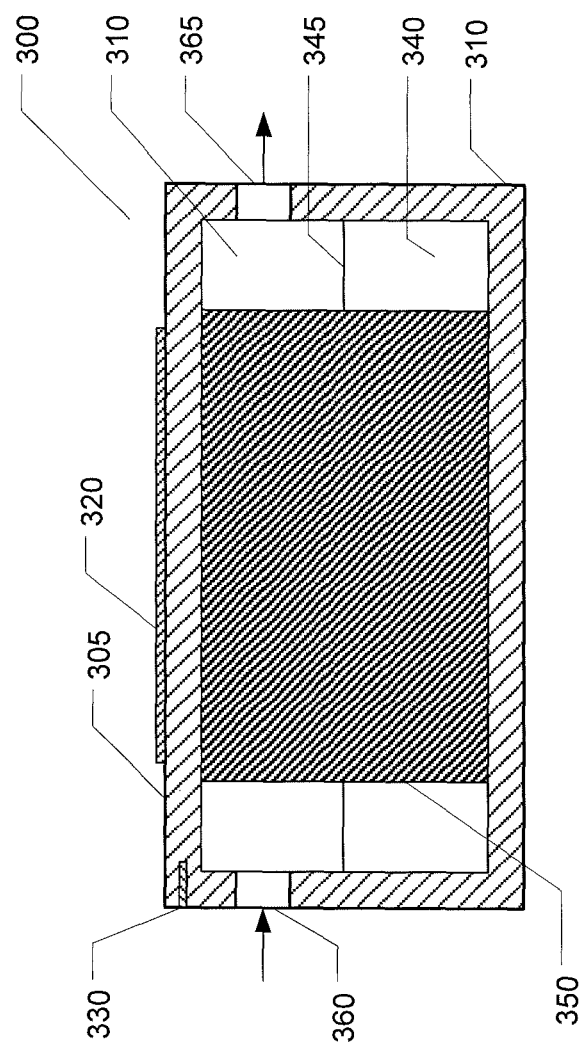
FIG. 2 is a longitudinal sectional view of saturator 300 of FIG. 1.
Figure 3:
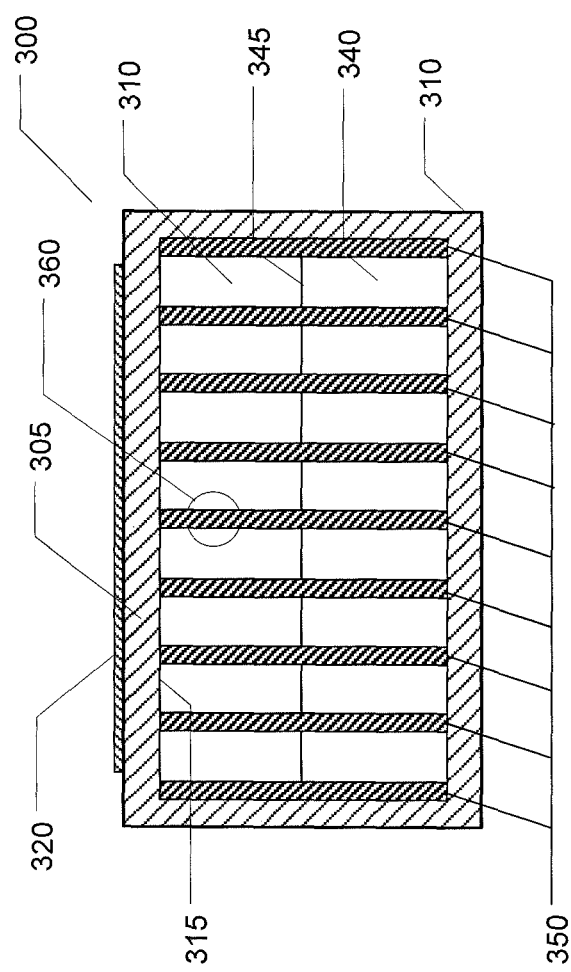
FIG. 3 is a sectional view of saturator 300 of FIG. 1 in a transverse direction to the direction of gas flow.

FIG. 1 illustrates a condensation particle detecting apparatus generally indicated at 90 according to the present disclosure. The apparatus 90 includes a pump, 100, to maintain a steady gas flow through the system and allow gas carrying suspended particles from source 200 to flow through, the pump speed being adjustable in order to adjust or control the rate of gas flow to a desired value. Source 200 can be the ambient atmosphere, the atmosphere of a clean-room, or simply a source of gas-borne particles being sampled into the system for detection. The apparatus 90 also includes a saturator, 300, to saturate the gas with vapor and a condenser, 400, to create a super-saturated vapor atmosphere in which vapor can condense on particles to form droplets for detection by the downstream detector, 600.

In addition, the apparatus 90 includes an electronic controller, 700, with the needed circuitry to receive output signal from various sensors in the system 90 and provide the needed control to operate the individual system components in a consistent and repeatable manner. Typical parameters that need to be monitored and controlled include temperature, flow rate, liquid level, and those pertaining to droplet detection by light scattering, such as the output power of the laser light source, sensitivity of the photo-diode or photomultiplier detector, gain and threshold settings for the detecting circuitry, among others. All system components such as pump 100, saturator 300, condenser 400, and detector 600 are provided with the requisite input and output lines 101, 301, 401, and 601 to communicate with controller 700 and maintain the individual system components to the desired operating point in the sensed and controlled parameters, controller 700 being provided with its own input and output lines 701 and 702 for communication and control purposes.

The apparatus of this disclosure is designed so that gas-borne particles will form the nucleus of condensation in a super-saturated vapor atmosphere to condense vapor on particles and form droplets for detection. The particles forming the nucleus of condensation are too small to be detected directly by light scattering detector 600. The particles are detected indirectly as a result of vapor having condensed on the particles to form droplets of a considerably larger size, thereby making the small non-detectable particles detectable by light scattering. In the ambient atmosphere, for instance, there are numerous particles smaller than about 100 nm in diameter. Such particles are generally very difficult to detect by an optical, light scattering approach. By growing the particles to a larger droplet size by vapor condensation and droplet growth and detecting the grown droplets by light scattering, the existence of the small condensation nuclei in the gas can be confirmed. The apparatus 90 is therefore also known by the name "condensation nucleus counter," or CNC. The saturator and condenser in a condensation particle counter can thus be viewed as a particle size magnifier helping to make a small, non-detectable particle into a large detectable droplet by vapor condensation and droplet growth.

The CPC is a unique instrument and an important device for aerosol measurement. In scientific usage, aerosol refers to a gas containing suspended particles. The most common gas is air. Other gases, such as nitrogen, helium, hydrogen, oxygen, etc. can also be the gaseous medium in which the particles are suspended. The CPC, therefore, is useful not only for airborne particle measurement, but for the measurement of gas-borne particles in general.

FIG. 2 is a longitudinal sectional view of saturator 300 along the direction of gas flow as indicated by arrows 302. A sectional view in the transverse direction perpendicular to the direction of gas flow is shown in FIG. 3. Saturator 300 is provided with an enclosure 305 with attached electric heater 320 and temperature sensor 330 in order to control the enclosure temperature to a desired set-point value. Enclosure 305 forms an envelope around chamber 310 in which a liquid is placed to generate vapor for saturating a gas flowing through the chamber. FIG. 3 shows a liquid working fluid 340 which is filled to level 345 in the chamber. In addition to the working fluid 340, which provides the source of vapor, a multitude of porous plates 350, preferably porous metal plates, is placed in the chamber and partially immersed in the liquid. The porous plates are positioned substantially parallel to the flow of gas through the chamber. By virtue of capillary surface tension, the interstitial pore space of the porous panels is filled with working fluid 340 including the portion of the porous panel in the gas-filled space above liquid surface 345. As a result, the porous panels are filled with liquid working fluid 340 thereby making the porous panels fully wetted by liquid. Since all parts of the system are in close thermal contact with one another, the entire assembly, including the enclosure 310, porous metal panels 350, and working fluid 340 contained therein are heated to substantially the same uniform temperature.

Enclosure 305 is provided with an inlet, 360, for the gas carrying suspended particles to enter and an outlet, 365, for the gas to exit. As gas carrying suspended particles flows through the gas flow passageways between the liquid-filled, wet porous panels 350, the gas is heated by the hot, wet porous panels 350. At the same time, liquid evaporating from the wet panel surface will generate vapor to saturate the gas (with suspended particles) with vapor. The gas, upon exiting the saturator thus becomes heated and is substantially saturated with vapor. The saturator is designed so that the gas will attain a selected temperature $T_1$ and is substantially saturated with vapor at that temperature upon its exit from the saturator. This vapor saturated gas with the suspended particles then flows into chamber 400 to create super-saturation for vapor condensation and droplet growth. Saturator 300 can also be designed with a pre-heater to pre-heat the gas to substantially the same temperature as the saturator. The gas so preheated can then be saturated with vapor as it flows along the liquid-filled, wet porous panels in the saturator. Either of the above approaches can be used to heat the gas and saturate the gas with vapor.

The design of saturator 300 in FIG. 2 and FIG. 3 shows heater 320 to be attached to the top of enclosure 310 to insure that the top of the enclosure is slightly warmer than the remaining parts of the saturator. Vapor evaporating from the liquid surface 345 and from the surface of the porous panels, 350, in the enclosure will thus encounter a slightly warmer inside surface 315 at the top and not condense there. Vapor condensing on the inside top surface 315 would form accumulated liquid which would fall back to liquid 340 below to cause splashing, which would generate small droplets that can be carried by the gas flow into the condenser to create a false particle count. For particle detection in a clean-room with low airborne particle concentration, a false count will contribute to the measurement error and must be avoided.

A multitude of porous panels 350 is provided in saturator 300 in order to provide a multitude of wet panel surfaces to generate vapor. By using a large number of closely spaced panels substantially parallel to the flow of gas as shown in FIG. 3, a very large wetted surface area can be created in a small physical volume, thus allowing a high volume of gas to flow through and be saturated with vapor. At low volumetric rate of gas flow, a single porous panel is sufficient. A single panel immersed in liquid will provide two wetted surfaces above the liquid from which the liquid can evaporate to generate vapor, which then diffuses into the gas stream flowing nearby. At higher gas flows, a multitude of plates are used to provide enough surface area for vaporization. In one implementation of the saturator, ten plates spaced 3 mm apart from each other have proven sufficient to achieve the desired vapor saturation results needed for the application. The parallel panels will thus make it possible to design a CPC 90 with a high volumetric flow rate of gas in order to detect particles having a low airborne concentration such as that in a clean-room.

Traditional CPCs are designed with the liquid evaporating from a wet-wall saturator with the gas flow passageway being surrounded by a porous material wall filled with the working fluid. The flow passageway can have a rectangular cross-section, as shown in U.S. Pat. No. 4,790,650, or a tubular flow passageway with a circular cross-section as shown in U.S. Pat. No. 6,829,044B2. In these traditional saturator designs, liquid can only evaporate from the wet rectangular or circular walls surrounding the gas-flow passageway with no additional surfaces being provided to generate vapor for saturating the gas.

In the vertical parallel panel design of the present disclosure additional evaporative surface areas are provided within the overall envelope of the gas-flow passageway walls to generate vapor for saturating the gas. This approach greatly increases the surface area that can be placed in the gas flow passageways to saturate a high rate of gas flow through the passageways. The design of this disclosure is also very flexible making it possible to increase the wet evaporative surface to as large an area as necessary in order to saturate the gas at any desired rate of gas flow. The lack of a suitable saturator with an adequate evaporative capacity has limited the maximum gas flow rate that can be achieved in the traditional CPC design in the past. Such flexibility is now provided in the saturating apparatus design of the present disclosure.

Figure 4:
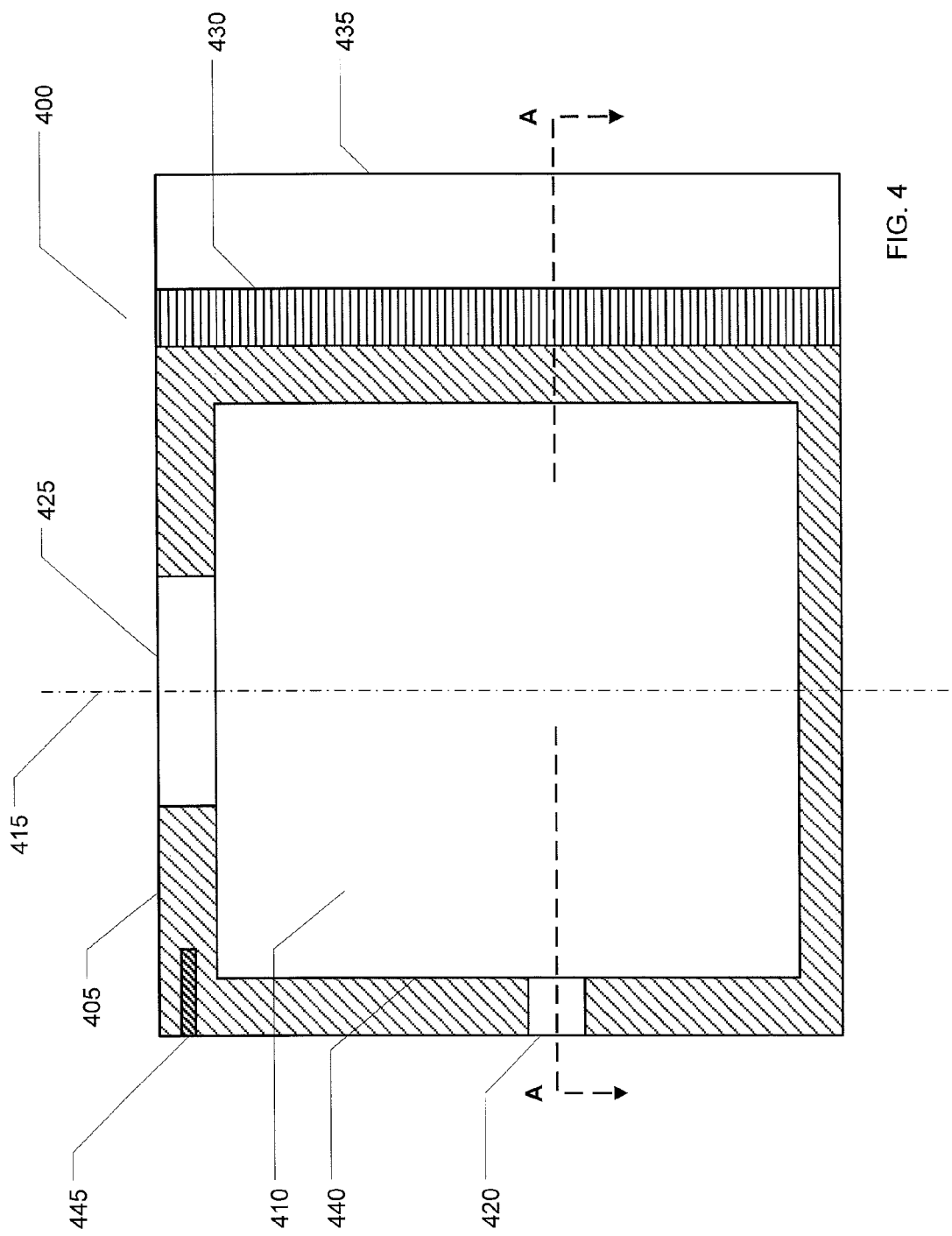
FIG. 4 is a vertical sectional view of condenser 400 of FIG. 1.

FIG. 4 shows the vertical sectional view of condenser 400 in one embodiment. The condenser is made from a rectangular shaped metal piece containing a cylindrically shaped chamber 410 with the chamber's axis 415 placed in a vertical orientation. Chamber 410 has an inlet 420 for a gas to enter and an outlet 425 for the gas to exit. Inlet 420 is located on the vertical side wall of the cylinder, while outlet 425 is located on a top wall. A thermoelectric cooling (TEC) module 430 is placed in close thermal contact with metal piece 405 to cool the metal piece to a desired operating temperature, $T_2$. Cooling is achieved by applying a DC voltage to cause a DC current of a specified polarity to flow through TEC module 430 to create the desired thermoelectric cooling effect. Heat generated by the thermoelectric cooling module is dissipated to the ambient by an extended surface heat exchanger, 435, by natural or forced convection. As a result, the metal piece and the metal wall 440 of chamber 410 are also cooled to substantially the same temperature $T_2$. A temperature sensor, 445, in contact with metal piece 405 senses the temperature of the metal piece. With the aid of controller 700, the electric power input to TEC module 430 can be varied to allow temperature $T_2$ to be controlled to a desired set-point value.

In some cases, the condenser 400 may need to be heated to a temperature above the surrounding environment in which the condenser is placed. In which case, the current flow can be reversed by applying a voltage having a polarity opposite to that needed for cooling. TEC module 430, therefore, can be placed in the heating mode working as a heat pump to pump heat from the surrounding environment to heat the condenser. Alternatively, a separate electric heater can be used to provide heating to the condenser, and keeping it at a temperature above the surrounding environment.

As the gas containing vapor and suspended particles flows through inlet 420 into the thermoelectrically cooled condensing chamber 410, the relatively warmer gas encounters the relatively cooler condenser chamber wall 440, thereby causing the relatively warmer gas to cool forming a gas stream having a non-uniform temperature distribution. The temperature distribution in the gas becomes non-uniform because the gas stream moving closest to the cold condenser wall 400 will lose more heat than gas streams that are farther away from the wall. At the same time, vapor in the gas will diffuse to the chamber wall 440 to condense on the wall. The vapor concentration in the gas will also become non-uniform since the gas stream moving closest to the wall would lose more vapor by condensation on the wall than streams that are farther away. As a result, the vapor concentration in the gas will also become non-uniform. This non-uniformly cooled gas stream having a non-uniform temperature and a non-uniform vapor concentration profile then mixes when the gas flow becomes turbulent thereby creating a mixture having a more uniform temperature and vapor concentration. The result is the formation of a super-saturated vapor atmosphere in which vapor can condense on particles to form droplets. The mixture then flows out of chamber 410 through outlet 425 to droplet detector 600 located downstream of condenser 400 as shown in FIG. 1.

The approach to creating vapor saturation by cooling and mixing a gas in a cold-wall chamber in the manner described above is previously unknown. The theoretical basis of such an approach will be explained more fully later in this disclosure.

Figure 5:
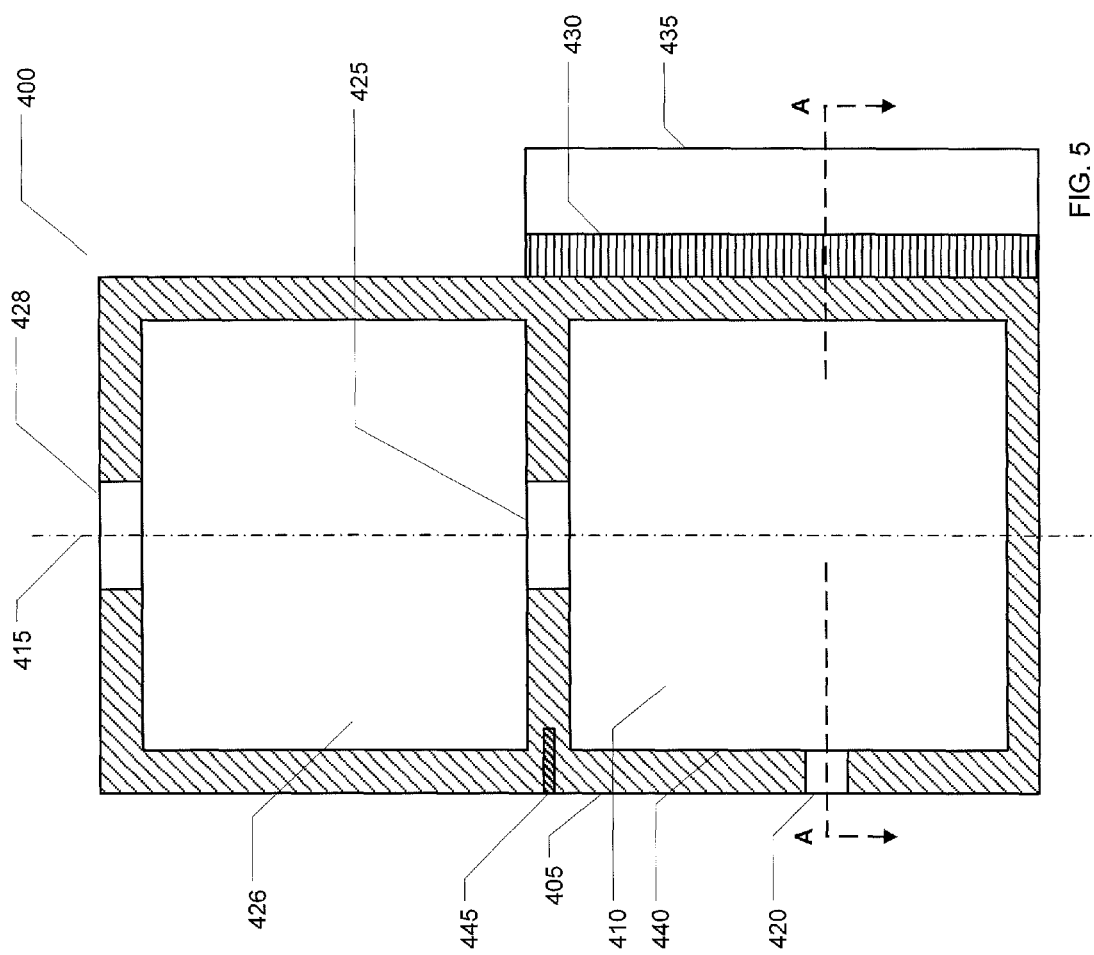
FIG. 5 is a sectional view of in another embodiment of a condenser.

An embodiment with additional features of the condenser 400 is shown in FIG. 5. The length of cylindrical chamber 410 is extended by providing a second condensing chamber 426 downstream of condensing chamber 410. Outlet 425 for chamber 410 then becomes the inlet for chamber 426. Outlet 425 is smaller in cross-sectional area than chambers 410 and 426, thus forming a restrictive flow passageway for the gaseous mixture from chamber 410 to flow through and enter chamber 426. The gas flow in this restrictive flow passageway is sufficient to create a turbulent gas jet downstream of the restriction. The fluid turbulence in the gas jet creates additional mixing to make the gas mixture in chamber 426 more homogeneously mixed than the mixture in chamber 420. In addition, chamber 426 provides additional volume for the gas to reside and flow through, thereby increasing the overall residence time of the mixture in chambers 410 and 426 to give the droplets more time to grow to a larger size prior their exit through outlet 428 with the gas flow to the downstream droplet detector 600.

Figure 6:
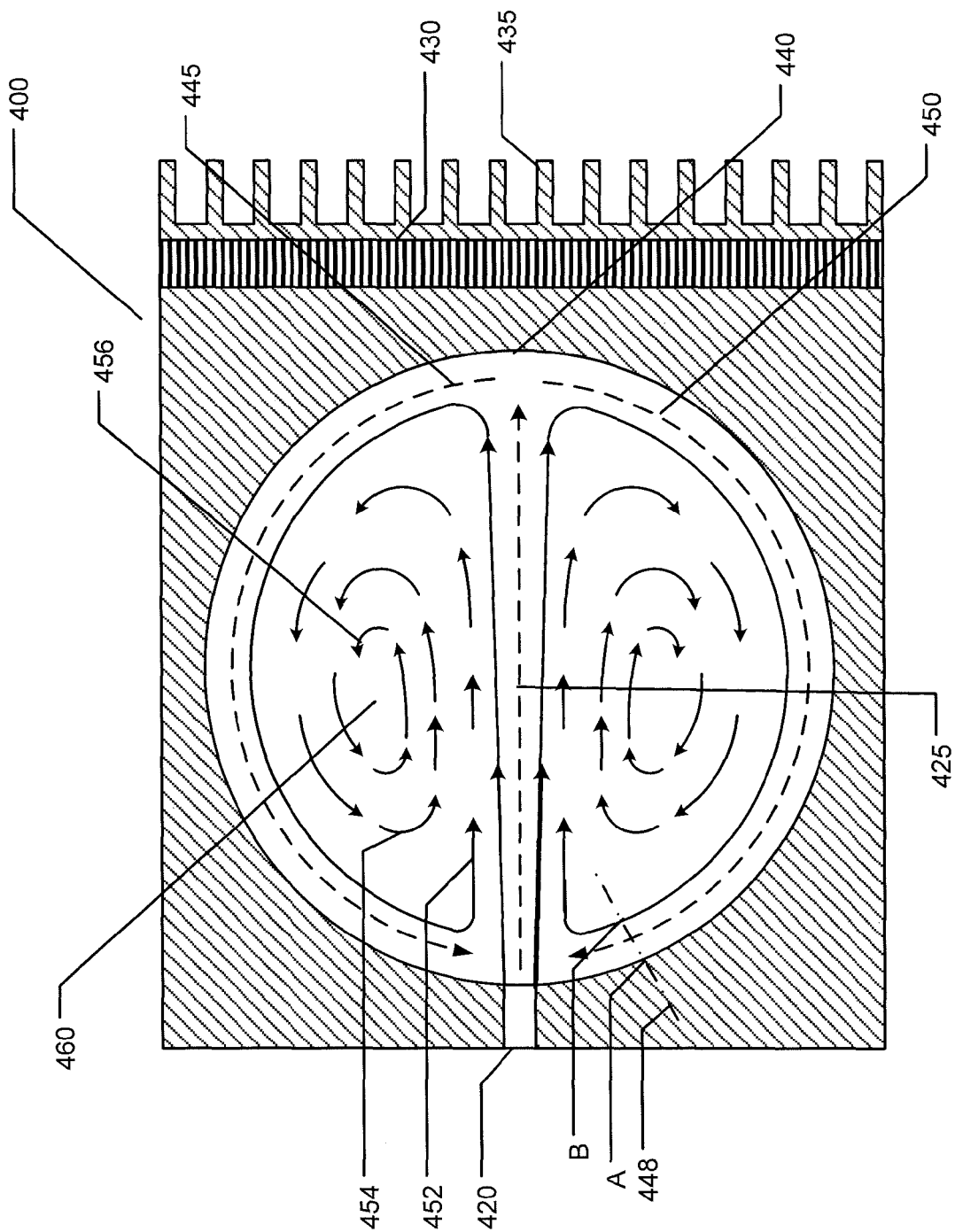
FIG. 6 is a sectional view of condenser 400 showing circulatory gas flow created by a gas jet impinging on the wall of a cylindrically shaped chamber in a perpendicular direction.

FIG. 6 is a horizontal sectional view of FIG. 4 showing the cylindrically shaped chamber 410 along section A-A of FIGS. 4 and 5. Thermoelectric module 430 and heat sink 435 are similarly labeled in both FIGS. 4 and 5 and FIG. 6. As the warm vapor laden gas with suspended particles enters through inlet 420, the gas with suspended particles forms a gas jet travelling along path 425 through the intervening cylindrical chamber space to impinge on the opposite wall of the chamber. Upon hitting wall 440 the gas jet is deflected side ways to create a circulatory gas flow along paths 445 and 450. As the gas flows along these paths, it loses heat to the adjacent cold condenser wall 440 by convection. At the same time, the vapor will also condense on the surface of the cold condenser wall. The condensed liquid will drain by gravity along the condenser wall to a liquid reservoir below, which is not shown. The condenser 400 is maintained at a relatively cooler temperature, $T_2$, compared to the temperature $T_1$ of saturator 300. At the end of the circulatory gas flow pathways, or streamlines, 445 and 450, the gas, having cooled by contact with wall 440, and having lost some vapor by condensation, will have a non-uniform temperature distribution across the streamlines. As used herein, flow paths and streamlines are synonymous terms in laminar flow, the fluid does not intermix. The fluid travels in a well defined path to form a well defined streamline. In turbulent flow, there is turbulent mixing of the fluid. In which case, the flow paths, or streamlines refer to the pathway or streamline of the mean flow. Superimposed on the mean flow pathway or streamline are turbulent eddies that cause the flow to move rapidly in the lateral direction. At the same time the partial pressure of vapor in the gas stream will also become non-uniformly distributed across the streamlines due to the varying amount of vapor that has diffused across the streamlines to condense on the wall of the cold-wall condenser. Upon reaching the end of flow paths 445 and 450, the remaining kinetic energy of the flowing gas stream will cause the gas stream to breakup into turbulent eddies, filling the space in the core of the circulatory gas flow with a turbulent mixture. The turbulent gas flow is in the turbulent core. The turbulent gas flow helps make the mixture become more uniformly mixed with a substantially uniform temperature and partial vapor pressure in the gas. The flow in this circulatory gas flow condenser is therefore in the form of a vortex flow with a relatively higher velocity gas flow circulating around a turbulent vortex core to produce the mixing needed for the vapor to become super-saturated and condense on particles to form droplets.

The gas flow pattern depicted in FIG. 6 is that from a gas flowing at a relatively high volumetric rate of flow through an inlet 420 with a relatively small cross-sectional area, thereby creating a high velocity gas jet with a high linear momentum in the direction of the gas jet. This high momentum gas jet upon traveling to the end of the circulatory flow paths 445 and 450 adjacent to the condenser wall would have lost some linear momentum due to fluid friction, but would still retain sufficient momentum for the gas to flow in the forward direction, causing it to spiral inward as shown by arrows, 452, 454, and 456, toward the center 460 of a vortex as depicted in the top half of FIG. 6. As the gas flow spirals inward toward the center 460, it will continue to shed turbulent eddies to dissipate the kinetic energy carried by the flow, thereby creating a turbulent region in the vortex core. The vortex flow depicted in the top half of FIG. 6 has a counter clockwise rotation. The vortex formed in the bottom half the FIG. 6 is similar to that in the upper half except the direction of rotation of the vortex is clockwise.

Figure 7:
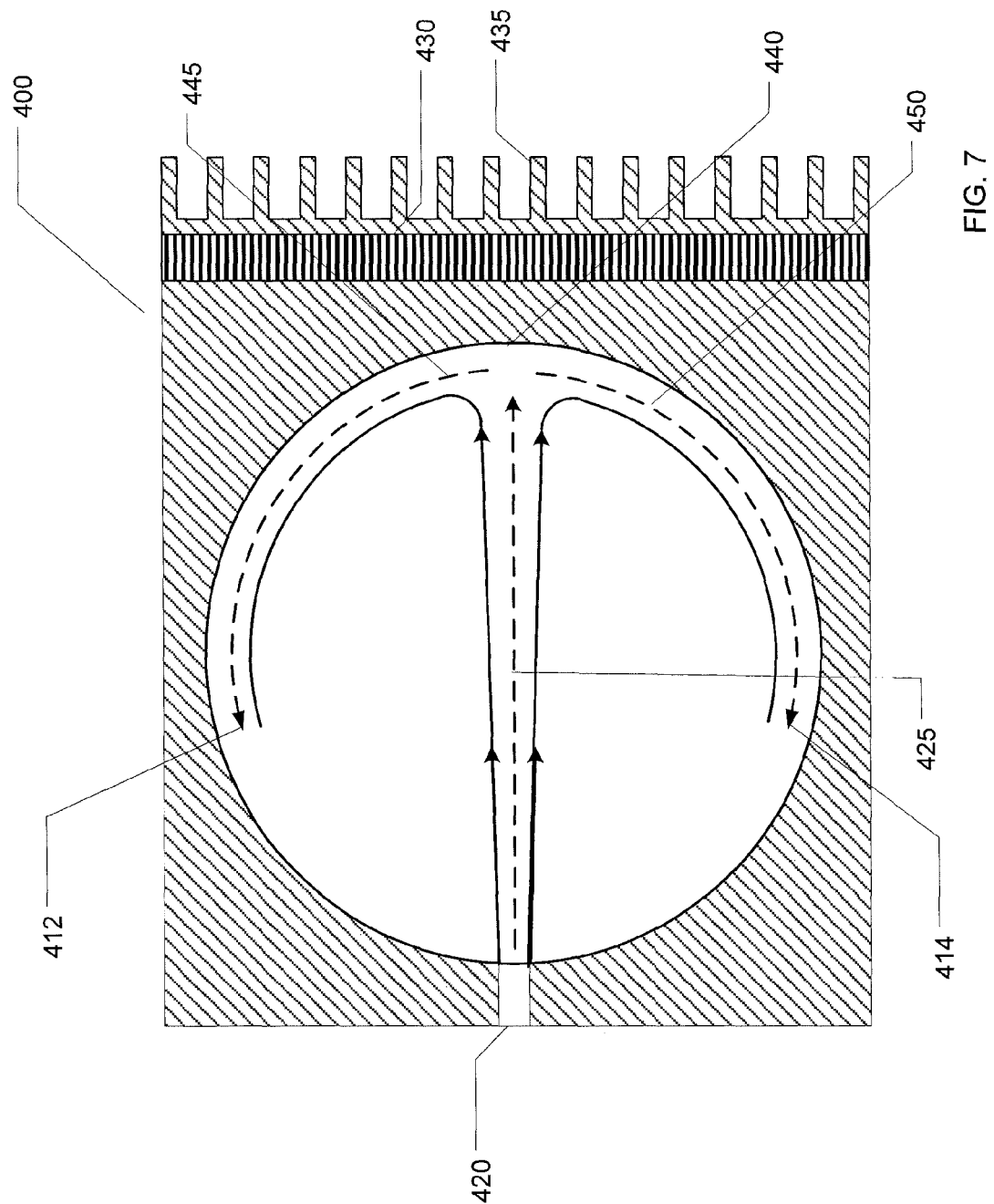
FIG. 7 is the same sectional view of condenser 400 as shown in FIG. 6 but illustrating a gas jet with small linear momentum creating a circulatory gas flow along the cold condensing wall ending with the flow becoming mixed prior to reaching the end of the full flow path along the cold condenser wall.

In contrast to the above, a gas entering the chamber at a relatively low volumetric rate of gas flow through an inlet with a relatively larger cross sectional area will carry less momentum. Such a gas would form a jet travelling through the cylindrical chamber as in FIG. 7 at a relatively low speed. The gas jet, upon hitting wall 440 would be deflected sideways to flow along paths 445 and 450 adjacent to the cold chamber wall 440. The momentum of the flowing gas stream is too low for it to flow beyond the end of the path at 412 and 414. Upon reaching the end of flow paths 412 and 414, the gas, having lost much of its forward momentum will flow to the vortex core region with much less turbulent mixing compared to that depicted in FIG. 6. Mixing will still occur, but with a lesser intensity than that depicted in FIG. 6.

To prevent the gas flow in chamber 410 in the circulatory gas flow condenser of FIG. 4 from flowing out of chamber 410 prior to sufficient mixing has taken place, the top of the chamber is provided with outlet 425 with a smaller cross-sectional area than that of the cylindrical chamber to confine the circulating gas flow in chamber 410 and cause it to mix prior to its exit from the chamber, thus helping the gas flowing out of the chamber to be uniformly mixed. As discussed earlier, a second chamber can also be provided as shown in FIG. 5 to provide additional volume for the mixture to undergo additional mixing and provide more residence time for the droplets to grow in the chamber.

The jet of gas issuing out of orifices 420 and 425 will be turbulent if the Reynolds number of the flow is larger than about 100. In comparison, the gas flow in a circular tube typically does not become fully turbulent until the flow Reynolds number exceeds 2300. The flow Reynolds number is defined as
Re=UDρ/μ where Re is the Reynolds number, U is the gas velocity, D is the diameter of the orifice or the tube, ρ is the gas density, and μ is the gas viscosity. So, fluid turbulence can be created with a gas flow velocity that is more than a factor to 10 smaller compared to a tube for a comparable diameter. This means good turbulent mixing can be achieved much more readily with a turbulent jet than by turbulent flow in a tube.

In various embodiments of the present disclosure including those shown in FIG. 4 through FIG. 9 and FIG. 13, the cross-sectional shape of the cylindrical chamber is generally circular, but other shapes, such as that of an ellipse, a square, a rectangle, and other polygonal shapes with straight interior surface walls, or a combination of shapes formed by straight and curved wall can also be used. The three-dimensional chamber also does not need to be cylindrical in shape as depicted in FIG. 4. Other chamber shapes such as the shape of a sphere, an ellipsoid, a pyramid, a cube, a rectangle with length, width and height that are not equal, and other polyhedral shapes formed by flat walls, or walls with some that are flat and some that are curved. Since the circulatory gas flow pattern can develop in a wide range of chamber shapes, the precise shape of the chamber is relatively unimportant, The required circulatory gas flow pattern can develop in many different chamber shapes and still suffice to provide the needed cooling and mixing to generate a super-saturated vapor in the chamber for condensation and droplet growth on particles.

The approach described above of using a circulatory gas flow to create a super-saturated vapor atmosphere in a cold-wall condenser for vapor condensation and droplet growth is fundamentally different from other approaches that have been used in the past for creating vapor super-saturation for condensation particle counting. Historically, particle counting by vapor condensation and droplet growth is based on adiabatic gas expansion to cool the gas and create a super-saturated vapor atmosphere for condensation and droplet growth to occur. The gas flow in such devices is intermittent. The historically important expansion type CPC, which has an intermittent gas flow, has largely been replaced by the modern continuous flow CPCs similar to that described in U.S. Pat. No. 4,790,650. In contrast to the expansion type CPC which uses water as a working fluid, the modern continuous flow CPCs are organic fluid based in which an organic working fluid such as alcohol is used to generate vapor for condensation, with butyl alcohol being the most widely used working fluid. An approach to adiabatic gas expansion for gas cooling in a continuous flow CPC is described in U.S. Pat. No. 6,980,284 in which a vapor saturated gas is expanded through a small diameter capillary tube under condition of high pressure drop to create sonic flow and adiabatic gas cooling in the capillary tube.

In recent years, there is an interest in returning to water as a working fluid because of its abundance and non-contaminating nature. Water is also considered an "environmentally friendly" substance to use in a measuring instrument such as the CPC. As pointed out in U.S. Pat. No. 6,712,881, water does not work well in the traditional continuous flow CPC, since water would diffuse too quickly to the cold condenser walls of the laminar flow condenser to cause the gas stream to be depleted with water vapor by an amount sufficient to prevent super-saturation to develop for vapor condensation and droplet growth. The laminar flow, cold wall condenser is therefore normally used with an organic working fluid, such as butyl alcohol, because the relatively lower molecular diffusivity of the higher molecular weight organic working fluid would prevent rapid vapor depletion thereby making it possible for vapor super-saturation to develop in the laminar flow stream for condensation and droplet growth.

U.S. Pat. No. 6,712,881 then describes a laminar flow CPC of a non-traditional design for use with water as a working fluid. In this non-traditional design, a hot, wet-wall condenser is used in a laminar flow condenser to generate vapor for diffusion into a cold laminar gas stream flowing through the condenser. Water vapor is added to the flowing cold gas during its passage through the hot wet-wall condenser to create super-saturation for vapor condensation and droplet growth. The apparatus has since become a commercially available device. Another approach to using water as a working fluid is the continuous flow device described in U.S. Pat. No. 5,803,338 in which two water-vapor saturated gas streams—one hot and one cold—are mixed to create a mixture stream having a super-saturated vapor to condense on particles and form droplets.

The CPC of the present disclosure is similar to the traditional alcohol based continuous flow CPC in one respect in that hot vapor-laden gas containing suspended particles is introduced into a cold wall condenser to create vapor super-saturation for condensation and droplet growth. Unlike the traditional laminar flow condenser of the traditional design, the condenser of the present disclosure uses a circulatory gas flow to cool the gas and create vapor super-saturation for condensation and droplet growth in a chamber under turbulent flow conditions, while the gas flow in the traditional continuous flow condenser is both laminar and uni-directional, thus non-circulatory. In addition, unlike the traditional laminar flow cold-wall condenser that works well only with an organic working fluid, but not with water, the circulatory gas flow condenser of the present disclosure works well both with water as a working fluid, as well as an organic working fluid, such as alcohol. Further, in contrast to the mixing CPC of U.S. Pat. No. 5,803,338, in which two water-vapor saturated gas streams—one hot and one cold—are mixed to create super-saturation for vapor condensation and droplet growth, the apparatus of the present disclosure uses only one gas stream in a single condenser chamber to create a non-uniform gas stream in terms of temperature and vapor partial pressure, which is then mixed thoroughly by fluid turbulence to create vapor super-saturation for condensation particle counting. The condensing apparatus of the present disclosure is therefore simpler, and easier to implement than the two-stream apparatus of U.S. Pat. No. 5,803,338. Other mixing type CPCs such as those described in U.S. Pat. Nos. 4,449,816 and 6,567,157 also use a hot and a cold gas stream and mix the two to create the needed super-saturation for condensation and droplet growth.

The approach to vapor condensation and droplet growth described in the present disclosure, therefore, has resulted in an apparatus that is nearly universal in the choice of working fluid for use in the apparatus. Almost any fluid including water and those with a higher molecular weight and a correspondingly lower molecular diffusivity than water can both be used. It has also simplified the mixing CPC design by using a single gas stream in a single condenser chamber to create a non-uniform temperature distribution in a single gas and cause the gas to mix to create a super-saturated vapor atmosphere in the chamber for condensation and droplet growth.

Figure 8:
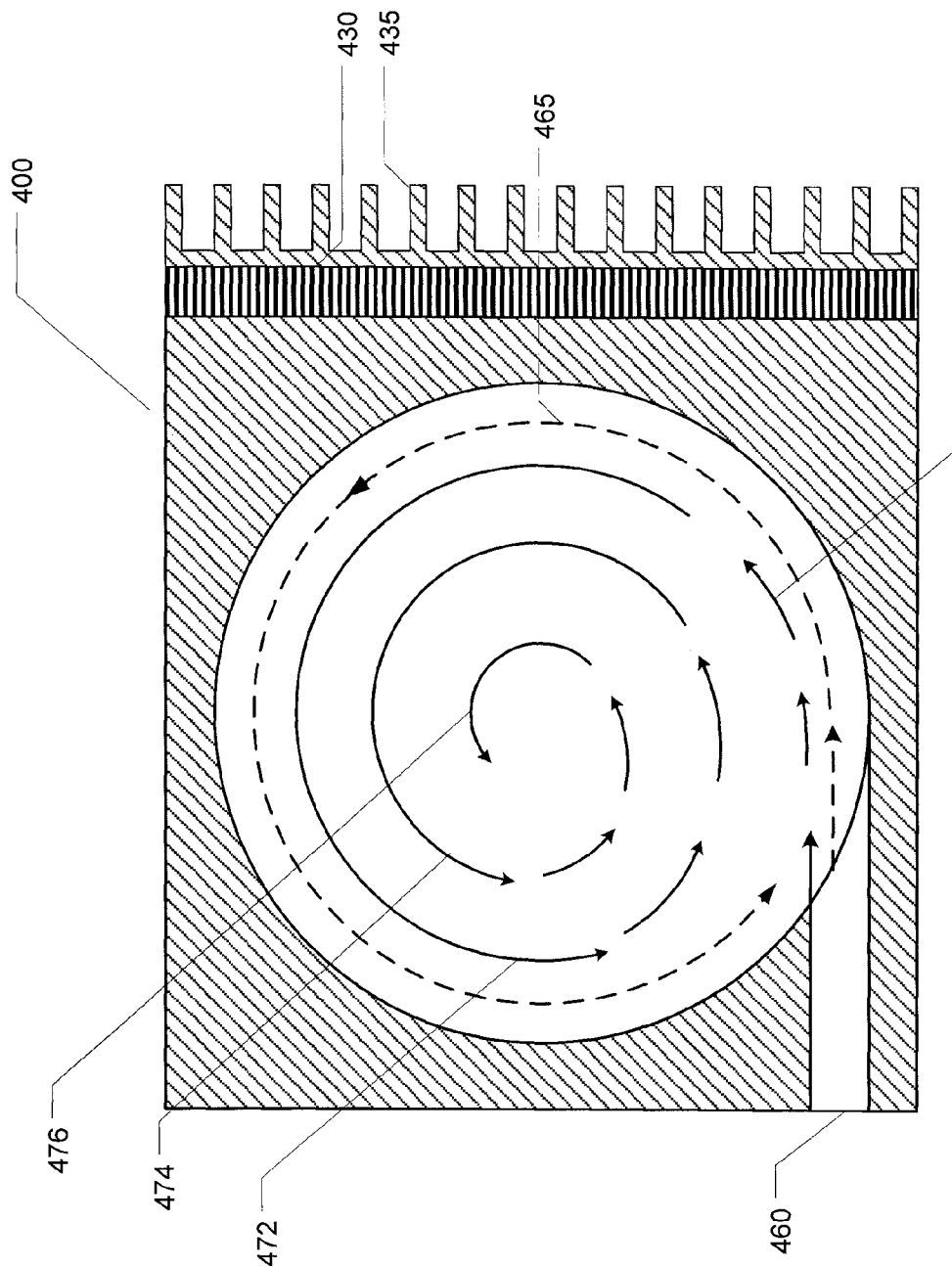
FIG. 8 is the same sectional view of condenser 400 as shown in FIG. 6 with a tangential gas flow inlet to create a circulatory gas flow in the chamber causing the gas to cool and mix leading to vapor super-saturation, condensation and droplet growth

In the embodiment of FIG. 6, the gas flow entering the condenser chamber through the inlet creates a gas jet impinging onto the wall of a cylindrical shaped condenser chamber in a normal, i.e. perpendicular direction. FIG. 8 shows an embodiment with circulatory gas flow by having the gas inlet 460 oriented to form a gas stream flowing along the periphery, i.e. the tangent of the circular section of the vertical cylindrical chamber. This tangential gas flow then moves along path 465 to cool the gas, causing it to mix with the incoming hot, vapor laden gas entering the chamber through inlet 460 to create a mixture having a super-saturated vapor atmosphere to condense vapor on particles and form droplets. The vortex flow that may develop in such a tangential inlet flow device is depicted by arrows, 470, 472, 474, and 476 in FIG. 8. As previously noted in the normal inlet condenser of FIG. 5, the vortex flow will develop only when the volumetric gas flow rate through the apparatus is sufficiently high and the cross-sectional area of the gas inlet is sufficiently small for a gas stream with a sufficiently high momentum to develop and create the vortex flow pattern in the condenser. At a lower volumetric gas flow rate through an inlet with a relatively large cross-sectional area, the full vortex flow may not form, but the relatively slow moving gas flow will still have sufficient momentum to create fluid turbulence for mixing and creating vapor super-saturation. The cylindrical chamber in both the one embodiment of FIG. 4 with a normal flow inlet and the other embodiment of FIG. 8 can have any cross-sectional shape, including circular, elliptical, square, rectangular, polygonal, among others. The preferred cross-sectional shape is circular.

Figure 9:
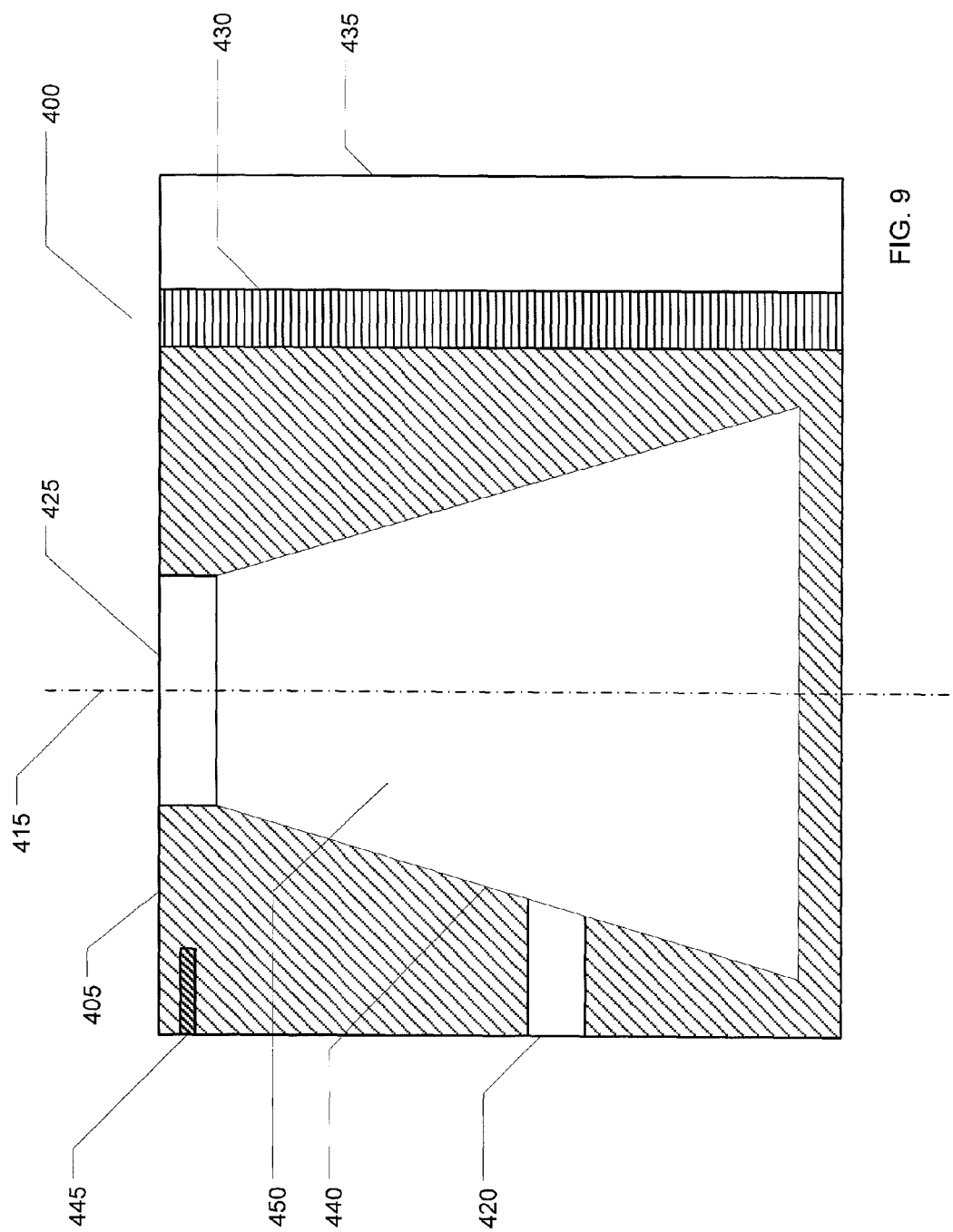
FIG. 9 is a vertical sectional view of a conical condenser.

FIG. 9 yet illustrates another example of a circulatory gas flow by locating gas inlet 420 on the side wall of a vertically oriented, conical chamber 450. Other than the chamber shape, all other aspects of the design are similar to the cylindrical chamber design of FIG. 4 with all similar parts being labeled with like reference characters. The conical shaped chamber can be used advantageously to improve the performance of the circulatory gas flow condenser and provide a more smooth aerodynamic flow transition from the larger conical base to the smaller flow outlet 425 on the top. Other orientations of the conically shaped chamber can also be used to achieve specific design advantages. Such advantages will become obvious to those skilled in the art of designing condensation particle counters after having studied the present disclosure. Therefore they will not be further described.

The process of using a circulatory gas flow condenser for creating vapor super-saturation, condensation and droplet growth can be analyzed theoretically to aid in the design of the actual apparatus. Although the complicated gas flow patterns in a circulatory gas flow condenser prevents an exact analysis to be made, an analysis made under certain simplifying assumptions can be helpful to improve the understanding of the operation of the circulatory gas flow condenser and the parameters affecting the ability of the device to create vapor super-saturation for condensation and droplet growth. Although the analysis described below is made under simplifying assumptions, the result is believed to be sufficiently accurate for many practical applications.

Figure 10:
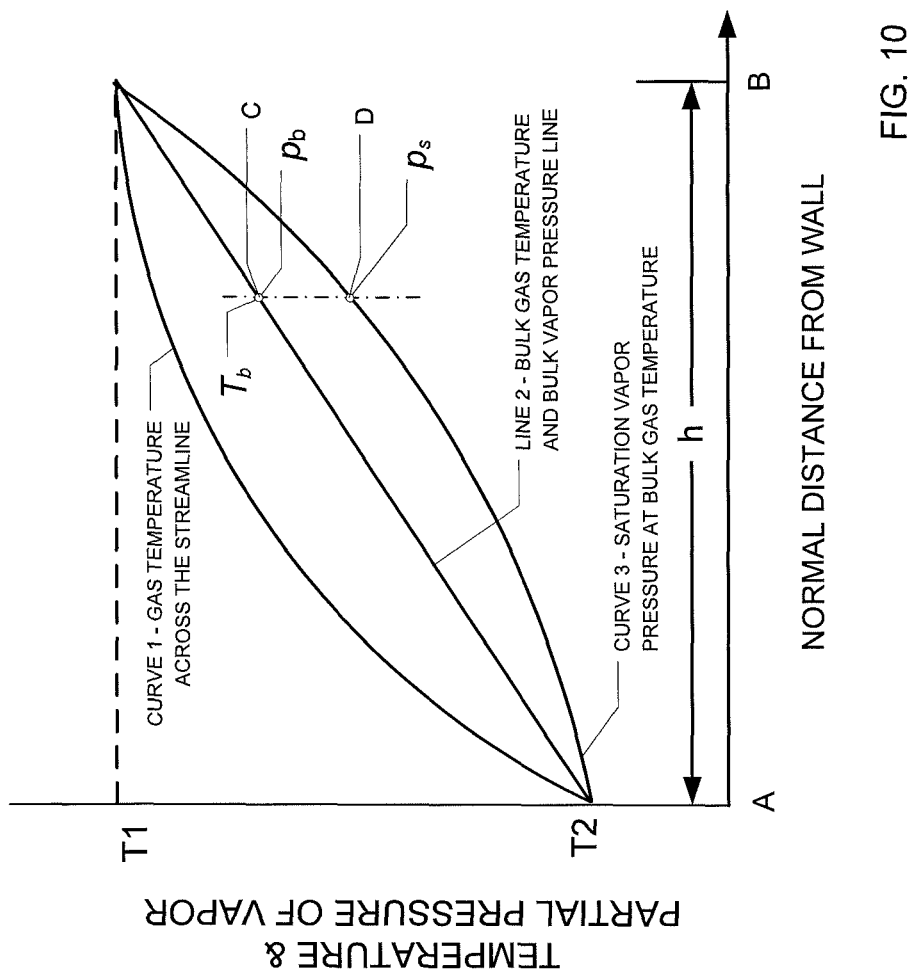
FIG. 10 is a graphical view illustrating the basis of the theoretical analysis leading to the results shown in FIG. 11.

FIG. 10 shows graphically the temperature distribution across the streamlines near the end of the flow path 450 in FIG. 6 along the direction of line 448, which is perpendicular to the cylindrical wall surface at that point. As one moves from point A to point B along line 448, one would move from the relatively cooler region close to the wall to the relatively warmer region further away from the wall. As depicted, the gas temperature at point A would be the same as the temperature of the wall, $T_2$. At the outer edges of the streamlines at point B and under suitable operating conditions one encounters circulating gas flow along this outer boundary of the gas flow away from the wall. Gas flowing along this outer boundary is not in contact with any cold wall surface. Therefore, it can lose heat only by turbulent mixing or thermal diffusion to the cooler stream flowing closer to the cold condenser wall. Again under suitable operating conditions, the gas stream along this outer boundary would lose very little heat or vapor to the cold condenser wall. As a result, the temperature at point B is not greatly different or is substantially the same as the temperature of the gas, $T_1$, entering the chamber through inlet 420. This is depicted by curve 1 in FIG. 10.

The line connecting the ends of Curve 1 is a straight line, Line 2, on which one can depict the bulk temperature, $T_b$, of the gas, following the turbulent mixing of the non-uniformly cooled gas stream in the turbulent vortex core, a region of space occupied by the sequences of arrow 452, 454, and 456, and the center, 460 of the vortex core in FIG. 6. The bulk temperature of a gas with a non-uniform temperature distribution is the temperature of the gas following thorough mixing of the gas under adiabatic conditions. Mixing is adiabatic if no heat is added or removed from the gas during the mixing process. Point C on Line 2 shows the bulk temperature, $T_b$, of the gas under one specific set of operating conditions of the apparatus.

As the gas flows along path 450 in FIG. 6, the stream line moving close to the cold wall surface will quickly cool to the temperature of the wall, $T_2$. Vapor will also condense from the gas stream, so that the vapor pressure of the gas will be the saturation vapor pressure of water at $T_2$. Gas flowing along streams at varying distances from the cold condenser wall will lose varying amounts of vapor by vapor diffusion as the individual streams reach the end of the path 450. The vapor pressure of water in the overall gas stream will thus also be non-uniform. In the turbulent vortex core, the main stream will be thoroughly mixed, creating a uniformly mixed stream having a bulk partial pressure of water, $p_b$, the bulk vapor partial pressure being the partial pressure of vapor in the bulk gas after thorough mixing without gaining or losing vapor during the process.

The rate of heat loss by a gas flowing adjacent to a cold wall is dependent on the thermal diffusivity of the gas and the nature of the gas flow. The rate of vapor loss depends on the molecular diffusion of the vapor in the gas and the nature of gas flow. The major resistance to heat and vapor loss to the cold condenser occurs in the laminar boundary sub-layer near the wall. In the laminar sub-layer, the rate of heat loss and vapor loss are proportional to the thermal diffusivity of the gas and the molecular diffusivity of vapor in the gas. For water vapor diffusion in air, the vapor diffusivity is not greatly different from the thermal diffusivity of the air. For simplicity, they are assumed to be equal. As a result, the same straight line, Line 2, connecting the ends of Curve 1, also depicts the bulk vapor pressure following turbulent mixing in the vortex core.

Curve 3 of FIG. 10 depicts the saturation vapor pressure of water at the bulk temperature, $T_b$, of the gas. Since vapor pressure increases more rapidly with increasing temperature, Curve 3 is a concave curve facing upward as depicted. This shows that the bulk vapor pressure, $p_b$, in the gas following mixing is higher than the saturation pressure, $P_s$, at the bulk temperature of the gas/vapor mixture. The ratio of $p_b$ and $p_s$ is the saturation ratio $$S = \frac{pb}{ps}$$

When S is less than 1.0, the gas is said to be under-saturated, and when, the gas S=1.0 is saturated. When S is greater than 1.0, the gas is said to be super-saturated. As shown in FIG. 10, the gas created by mixing a stream having a non-uniform temperature and vapor concentration is super-saturated.

Figure 11:
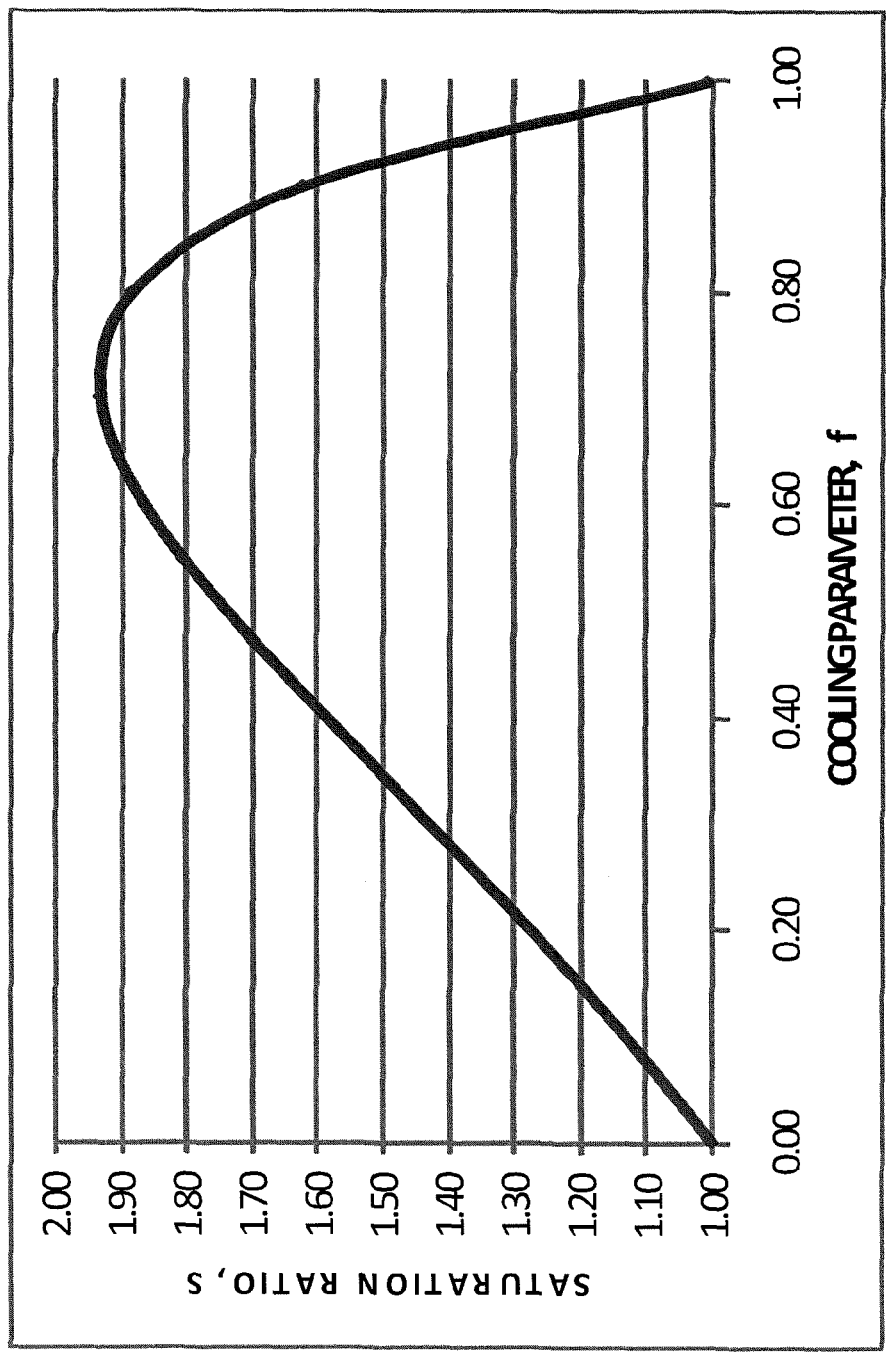
FIG. 11 is a graphical view illustrating the theoretical saturation ratio, S created in the circulatory gas flow condenser of the present disclosure showing the dependence of S on the cooling parameter, f.

FIG. 11 shows the result of a theoretical analysis based on the above approach. The theoretically calculated saturation ratio, S, is plotted against the cooling parameter, $$f = \frac{T1 - Tb}{T1 - T2}$$

where $T_1$ is the temperature of the saturated gas entering the condenser, $T_2$ is the temperature of the condenser wall, and $T_b$ is the bulk temperature of the cooled gas produced by the circulatory gas flow along the cold wall condenser.

The result of the above analysis shows that if the volumetric rate of gas flow through the condenser is too high, and the residence time of the gas in the circulatory gas flow condenser is too short, there is insufficient time for the gas flowing through the condenser to be cooled to a significantly lower temperature. In which case, $T_b \approx T_1$, f≈0, and S≈1.0 as shown in FIG. 11. Similarly, if the volumetric rate of gas flow through the condenser is too small, and the residence time of the warm vapor-saturated gas flowing into the chamber is too long, the gas would have cooled significantly and substantially to the same temperature as the condenser wall, i.e. $T_2$. In which case, $T_b \approx T_2$, f≈1.0, S≈1.0. Again, so super-saturation can develop, as shown in FIG. 11.

The result of FIG. 11 shows that super-saturation can develop only when there is partial cooling of the gas to an intermediate temperature, so that $T_2 < T_b < T_1$, or 0<f<1.0, and that the maximum super-saturation is developed when f≈0.7 for the specific example shown. Thus to develop maximum super-saturation for condensing vapor on the smallest particle size possible, the condenser chamber should be designed to achieve approximately 70% of the maximum cooling possible.

Figure 12:
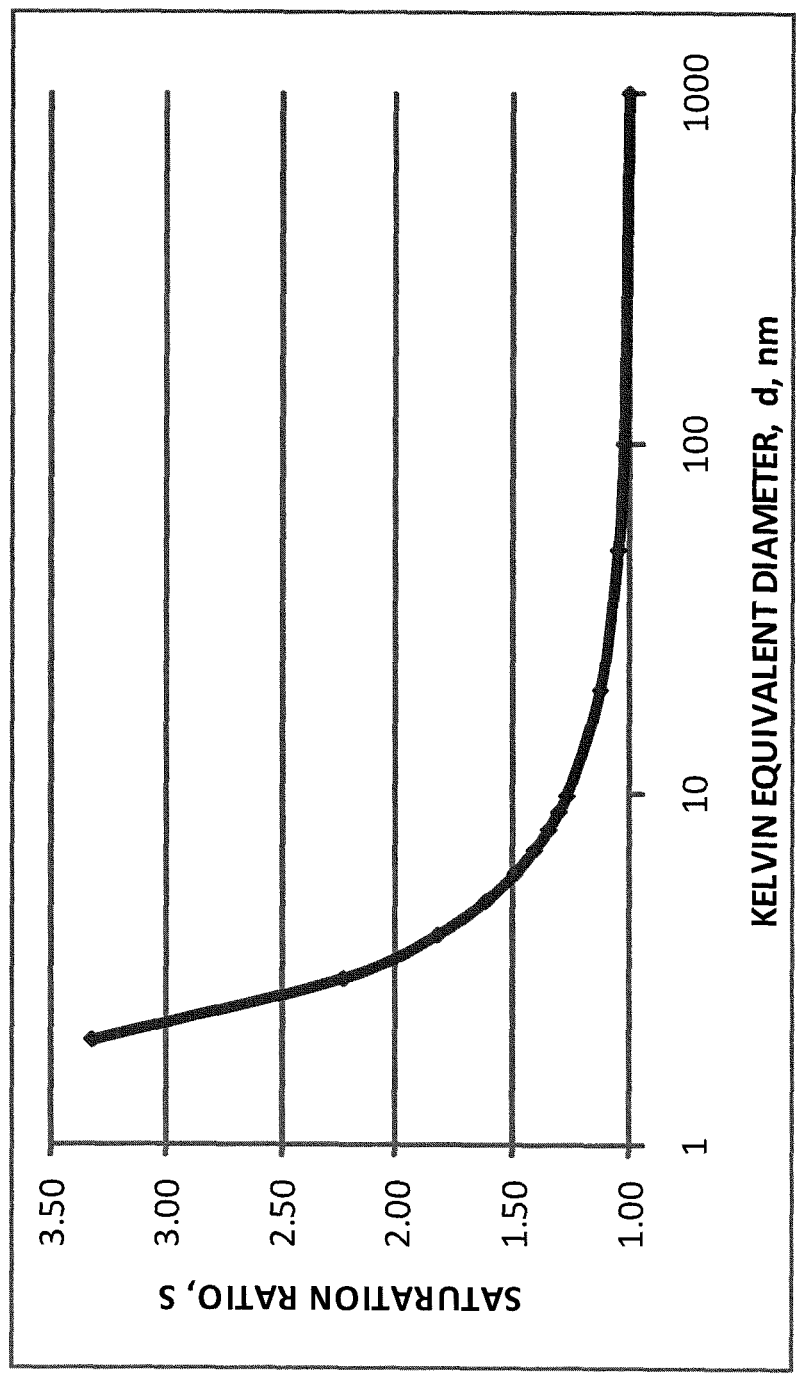
FIG. 12 is a graphical view illustrating the theoretical relationship between the saturation ratio, S, and the minimum diameter, d, of particles on which vapor will condense to form droplets for detection according to the Kelvin equation, with the diameter, d, being commonly referred to as the Kelvin equivalent diameter.

The relationship between the saturation ratio, S, and the minimum diameter, d, of particles on which vapor will condense to form droplets is governed by the Kelvin equation, $$S = \frac{P}{Ps} = \exp\left(\frac{4\sigma M}{\rho R T d}\right)$$

where σ is the surface tension of the liquid working fluid, M is its molecular weight, Σ is its density, R is the gas constant of the gas, T is the temperature, and d is commonly referred to as the Kelvin equivalent diameter. FIG. 12 shows the relationship between the saturation ratio and the Kelvin equivalent diameter for water. The result shows that the saturation ratio needed to cause vapor condensation on 10 nm diameter particles is S=1.27. For condensation on 5.0 nm particles, a saturation ratio of S=1.62 is needed and to condense vapor on 2.0 nm particles, a saturation ratio of S=3.31 would be necessary.

Like most analyses, the analysis made in this disclosure is not exact, and can be improved using more sophisticated methods. However, the ability of the circulatory gas flow condenser to create vapor super-saturation for condensation on particles does not depend on the accuracy or even the validity of the method used in the analysis. Laboratory experiments have shown that vapor super-saturation is indeed achieved and that the device of this invention is effective in creating vapor super-saturation for condensation particle counting using water as a working fluid, as well as an organic working fluid with higher molecular weight and correspondingly lower molecular vapor diffusivity than water.

Figure 13:
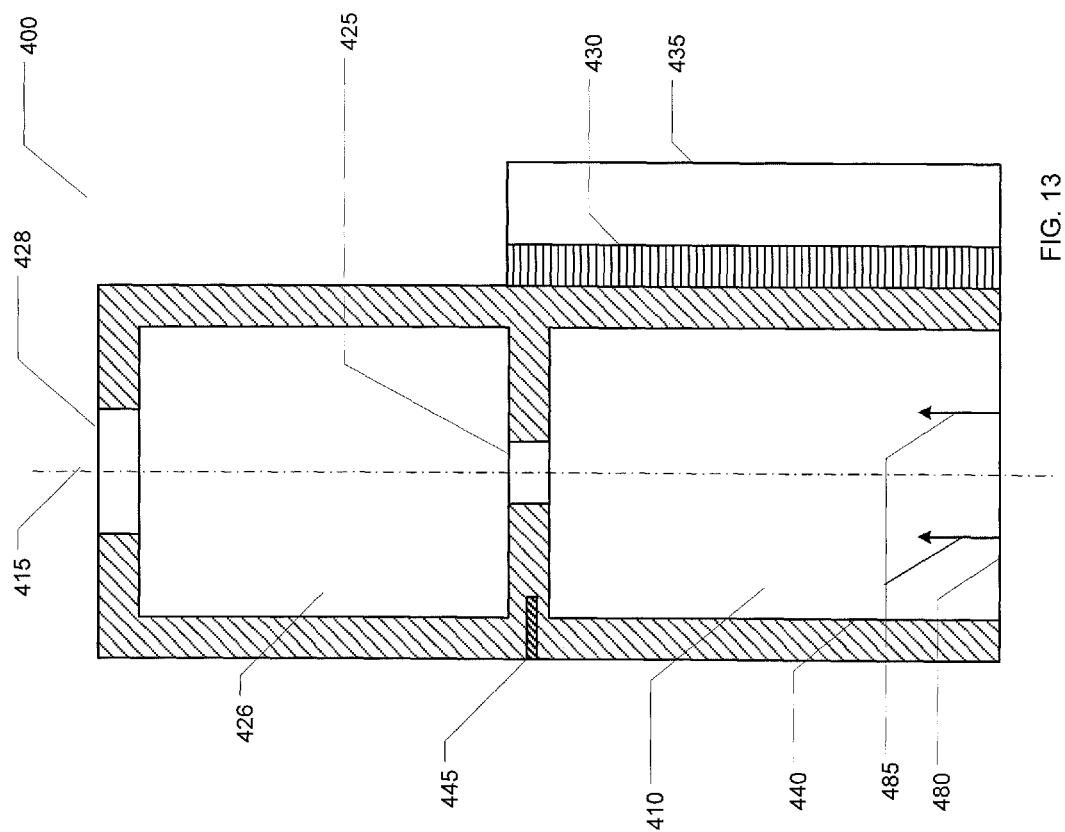
FIG. 13 is a sectional view of another embodiment of a condenser

FIG. 13 shows yet another approach to creating vapor super-saturation for condensation on particles to form droplets for detection and/or counting. FIG. 13 is similar to FIG. 5 except gas cooling is accomplished by a laminar gas stream flowing in a cold tube. In this embodiment, warm gas containing vapor and particles is introduced into a cooler tubular shaped chamber 410 with a generally circular cross-section. Upon entry into chamber 410 through inlet 480, the gas flows upward in the chamber as indicated by arrows 485. This flowing gas then loses heat by thermal diffusion to the cold chamber wall. At the same time vapor is lost to the wall by molecular diffusion and condensation on the wall. Streamlines that are close to wall 440 will lose heat and vapor more quickly than those that are farther away. As a result, the temperature of the gas and the partial pressure of vapor in the gas will become non-uniform as the gas flows upward in the chamber Upon reaching the end of the chamber, this non-uniformly cooled gas with a non-uniformly distributed vapor partial pressure in the gas then flows out of chamber 410 through flow restriction 425 to form a turbulent gas jet in chamber 426. The turbulence causes the gas to mix, thus making both the gas temperature and the vapor partial pressure in the gas more uniform, resulting in the creation of a super-saturated vapor which condenses on particles and forms droplets. The process is similar to that in the circulatory gas condenser of FIG. 4 except in the preferred embodiment of FIG. 4, cooling and mixing of the gas takes place in a single chamber, whereas in the embodiment of FIG. 13 two separate chambers are used, one for gas cooling and the other for mixing.

The embodiment of FIG. 13 is equivalent to that of adding a mixing chamber downstream of a conventional laminar flow cold-wall condenser. While the traditional laminar cold wall condenser by itself cannot create vapor super-saturation to form droplets when water is used as the working fluid as discussed in U.S. Pat. No. 6,712,881, the embodiment of FIG. 13 has made it possible to create a super-saturated vapor to condense on particles and form droplets for counting when water is used as the working fluid.

We have described in this disclosure various approaches to creating vapor super-saturation for condensation particle counting using a wide range of working fluids including water and chemical substances with a higher molecular weight and a lower vapor diffusivity than water. This disclosure will enable individuals skilled in the art of condensation particle counter design to use the principle described herein to create CPC designs beyond those described in the present disclosure. These designs, therefore, will not be further described or discussed.

Although the present invention has been described with reference to preferred embodiments, workers skilled in the art will recognize that changes may be made in form and detail without departing from the spirit and scope of the invention.

What is claimed is:

1. An apparatus for saturating a gas containing particles with vapor for said vapor to condense on said particles to form droplets for detection, said apparatus including a chamber for being partially filled with a liquid to form a liquid surface in said chamber, said chamber including an inlet positioned on a first chamber wall for said gas to enter and fill the space above said liquid surface, and a plurality of parallel porous planar panels partially immersed in said liquid to accept liquid into the porous panels, thereby permitting said liquid to evaporate from said wetted porous panels for forming vapor in said gas above the liquid surfaces, said chamber including an outlet positioned on a second chamber wall for said gas carrying said vapor to exit said chamber.

2. The apparatus of claim 1, wherein said porous panels are spaced apart to provide more than one passageway for said gas to flow through, with said wetted porous panels forming vertical side walls of said passageways to evaporate liquid and form vapor to saturate said gas flowing through said passageways.

3. The apparatus of claim 1, wherein said chamber has a mechanism for keeping a top portion of the chamber warmer than a lower portion of the chamber.

4. The apparatus of claim 1 and further comprising a droplet detector.

5. The apparatus of claim 4 wherein the droplet detector comprises an optical, light scattering detector.

6. The apparatus of claim 1 including an adjustable-speed pump to adjust a rate of flow of said gas through said inlet into said chamber to a selected value.

* * * * *